(12) United States Patent
Stcyr (10) Patent No.: US 9,855,054 B1
(45) Date of Patent: Jan. 2, 2018

(54) NOSE BLEED ARREST IMPLEMENT

(71) Applicant: Tony Stcyr, Griffin, GA (US)

(72) Inventor: Tony Stcyr, Griffin, GA (US)

( * ) Notice: Subject to any disclaimer, the term of this patent is extended or adjusted under 35 U.S.C. 154(b) by 288 days.

(21) Appl. No.: 14/739,516

(22) Filed: Jun. 15, 2015

(51) Int. Cl.
*A61M 29/00* (2006.01)
*A61B 17/132* (2006.01)
*A61B 17/12* (2006.01)

(52) U.S. Cl.
CPC .......... *A61B 17/132* (2013.01); *A61B 17/12* (2013.01); *A61B 2017/12004* (2013.01)

(58) Field of Classification Search
CPC .... A61F 13/2005; A61F 13/126; A61F 13/20; A61F 13/2022; A61F 13/2051; A61F 2013/00463; A61F 2013/00476; A63B 71/085; A63B 2071/088; A63B 2209/00; A63B 2071/086
USPC .................. 606/191, 196, 201; 128/859, 861
See application file for complete search history.

(56) References Cited

U.S. PATENT DOCUMENTS

| | | | |
|---|---|---|---|
| 1,701,616 A * | 2/1929 | Gross .................. | A61B 17/244 606/161 |
| 2,163,211 A * | 6/1939 | Wolf ........................ | A46B 9/04 15/110 |
| 2,550,190 A * | 4/1951 | Greenberg ......... | A46B 11/0003 15/167.1 |
| 3,342,183 A | 9/1967 | Edenbaum | |
| 4,457,756 A | 7/1984 | Kern et al. | |
| 4,791,941 A * | 12/1988 | Schaefer .............. | A63B 71/085 128/861 |
| 4,820,266 A | 4/1989 | Berry | |
| 5,383,891 A | 1/1995 | Walker | |
| 5,391,179 A | 2/1995 | Mezzoli | |
| 5,546,964 A | 8/1996 | Stangerup | |
| 5,584,822 A | 12/1996 | Lively et al. | |
| 5,787,540 A * | 8/1998 | Hirschmann ........ | A46B 5/0075 15/167.1 |
| D406,890 S | 3/1999 | Doyle | |
| 6,171,323 B1 * | 1/2001 | Potti .................... | A61B 17/244 600/570 |
| 6,709,443 B1 | 3/2004 | Rix | |
| 7,108,706 B2 | 9/2006 | Hogle | |
| 7,207,333 B2 | 4/2007 | Tohara | |
| 2004/0073299 A1 | 4/2004 | Hudson et al. | |
| 2004/0194788 A1 | 10/2004 | Sweet | |
| 2006/0058821 A1* | 3/2006 | Jansheski ............. | A61B 17/244 606/161 |
| 2006/0068364 A1 | 3/2006 | Struck | |
| 2009/0235474 A1* | 9/2009 | Seigel ............... | A46B 15/0055 15/111 |
| 2013/0274787 A1 | 10/2013 | Bruce | |

* cited by examiner

*Primary Examiner* — Katherine M Shi
(74) *Attorney, Agent, or Firm* — Robert C. Montgomery; Montgomery Patent & Design (57) ABSTRACT

A nosebleed arrest element is placed into a human mouth to alleviate bleeding from a nose. An upper portion of the device is placed between an interior portion of an upper lip and the gingiva of a crest of a maxillary bone. Placement of the device provides sufficient pressure upon subjacent arterial passageways to stem a flow of blood. A lower portion of the device protrudes from the mouth of a user. The lower portion is provided with a grasp catch to obviate swallowing of the device as a whole and to assist with maneuvering and removal of the device.

16 Claims, 6 Drawing Sheets

NOSE BLEED ARREST IMPLEMENT

RELATED APPLICATIONS

There are no current co-pending applications.

FIELD OF THE INVENTION

The present invention relates generally to an implement capable of being placed within a nasal cavity of a patient to arrest a nosebleed.

BACKGROUND OF THE INVENTION

Those of us that suffer from frequent nosebleeds have our favorite method for stopping them. One (1) method that finds success with many nosebleed sufferers is that of pressure against the front upper lip and gum area. A person may simply press their finger between their lip and gum while pressing firmly up against the nose. There is a blood vessel which runs against the upper lip, and pressure against it reduces blood flow, and allows the blood to clot. Many people have found that placing an object such as a rolled up piece of paper, a paper towel, gauze, tissue, or the like, produces the same effect. However, such materials are not often easy to find. Additionally, it is sometimes somewhat difficult to remove the material afterwards. Accordingly, there exists a need for a means by which nosebleed sufferers can be provided relief using the lip pressure technique, in a manner which addresses the above shortcomings. The use of the nosebleed arrest implement provides most users the ability to stop a nosebleed in a matter of seconds, in a manner which is quick, easy, and effective.

SUMMARY OF THE INVENTION

The inventor has recognized the aforementioned inherent problems and lack in the art and observed that there is a need for a quick and easily obtainable device that effectively slows down and arrests a nosebleed.

In one (1) embodiment, the device is in the configuration of a implement having an upper member having a thickness, a height, and a width and stem centrally located on a lower end of the upper member, also having a thickness, a height, and a width. The upper member is capable of being inserted into an area of a mouth between an upper lip and a gingiva on a crest of a maxillary bone to assist in arresting a flow of blood from a nasal cavity by application of restrictive pressure upon arterial passageways resulting from insertion of the upper member. The stem is configured such that the stem length extends away from the mouth when the upper member is properly positioned and aids in grasping and placing the upper member in the proper location and also for providing additional pressure.

In another embodiment, the upper member is fabricated from a water-soluble material.

In another embodiment the upper member and stem are configured from a unitary material. In such an embodiment, both the upper member and stem are fabricated from a water-soluble material.

Both the upper member and the stem have a posterior side, an anterior side, an upper side, a lower side, a first end, and a second end.

In another embodiment, the upper member is configured to be a curvilinear polyhedron and the stem is configured to be a linear polyhedron. In another embodiment, the stem second end terminates in a semicircular profile.

In another embodiment, the upper member is configured to have a thickness between the posterior side and the anterior side that tapers downward from the upper side to the lower side.

In another embodiment, the first end and second end of the upper member are configured to be an arcuate profile such that a greater amount of material is disposed along a midline of said length and a lesser amount of material along an upper edge thereof and a lower edge thereof.

Further advantages of the present disclosure will become apparent from a consideration of the drawings and ensuing description.

BRIEF DESCRIPTION OF THE DRAWINGS

The advantages and features of the present disclosure will become better understood with reference to the following more detailed description and claims taken in conjunction with the accompanying drawings, in which like elements are identified with like symbols, and in which:

DESCRIPTIVE KEY 10 nosebleed arrest implement
20 upper member
22 anterior surface
24 posterior surface
26 upper edge
28 lower edge
32 first end
34 second end
36 upper member first thickness
37 upper member second thickness
38 length
42 upper member height
50 stem
52 stem thickness
54 stem width
55 stem first end
56 stem second end
58 stem height
70 alternate device
72 first member
74 first member length
76 first member diameter
78 catch
82 connector

DETAILED DESCRIPTION OF THE PREFERRED EMBODIMENT

Figure 6:
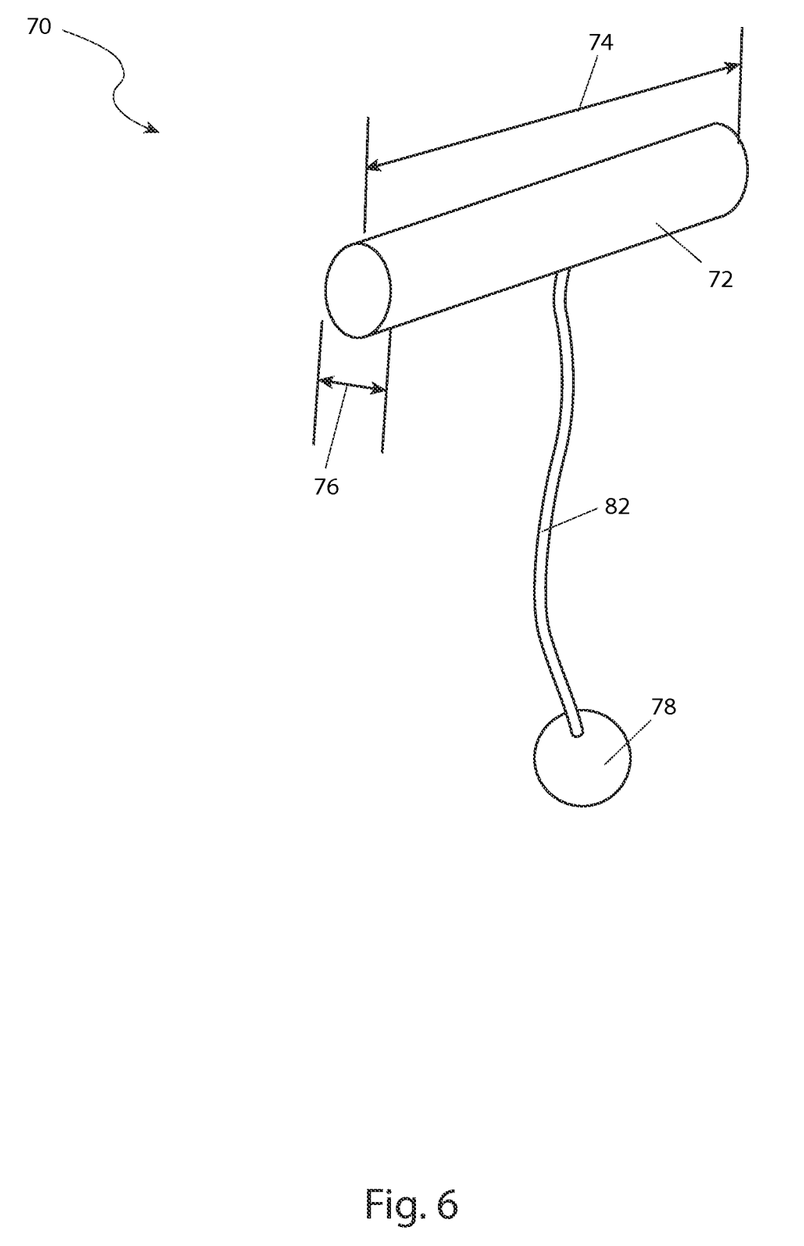

In accordance with the invention, the best mode is presented in terms of the described embodiments, herein depicted within FIGS. 1 through 5, and an alternate embodiment, herein depicted within FIG. 6. However, the disclosure is not limited to the described embodiments and a person skilled in the art will appreciate that many other embodiments are possible without deviating from the basic concept of the disclosure and that any such work around will also fall under its scope. It is envisioned that other styles and configurations can be easily incorporated into the teachings of the present disclosure, and only certain configurations have been shown and described for purposes of clarity and disclosure and not by way of limitation of scope.

It can be appreciated that, although such terms as first, second, etc. may be used herein to describe various elements, these elements should not be limited by these terms. These terms are only used to distinguish one (1) element from another element. Thus, a first element discussed below could be termed a second element without departing from the scope of the present invention. In addition, as used herein, the singular forms "a", "an" and "the" are intended to include the plural forms as well, unless the context clearly indicates otherwise. It also will be understood that, as used herein, the term "comprising" or "comprises" is open-ended, and includes one (1) or more stated elements, steps or functions without precluding one (1) or more unstated elements, steps or functions. Relative terms such as "front" or "rear" or "left" or "right" or "top" or "bottom" or "below" or "above" or "upper" or "lower" or "horizontal" or "vertical" may be used herein to describe a relationship of one (1) element, feature or region to another element, feature or region as illustrated in the figures. It should be understood that these terms are intended to encompass different orientations of the device in addition to the orientation depicted in the figures. It should also be understood that when an element is referred to as being "connected" to another element, it can be directly connected to the other element or intervening elements may be present. In contrast, when an element is referred to as being "directly connected" to another element, there are no intervening elements present. It should also be understood that the sizes and relative orientations of the illustrated elements are not shown to scale, and in some instances they have been exaggerated for purposes of explanation.

The present invention describes a nosebleed arrest implement (herein referred to as the "device") 10, which provides a means to stop a flow of blood from a nasal cavity of a user by the application of restrictive pressure upon certain arterial passageways in proximity to a crest of a maxillary bone resulting from the insertion of an upper member 20 of the device 10 into an area between the upper lip and the gingiva on the crest of the maxillary bone. In the ensuing discussion, any reference to a back, posterior, or rear, will indicate that portion of the device 10 placed against the gingiva, while the front, or anterior, will indicate that portion placed against the interior of the lip. It should be noted that since the size of the users to which the device 10 may be useful can vary considerably, there must be a range of sizes implicit in any embodiment of the device 10 without limiting the scope of the invention. An alternate device 70, having a cylindrical first member 72 is provided with a catch 78 and a connector 82 for removing the alternate device 80 from the user's oral cavity after use.

Referring now to FIGS. 1 through 5, according to the preferred embodiment of the present invention are disclosed. The apparatus 10 includes an upper member 20 and a stem 40. In a preferred embodiment, the upper member 20 and the stem 50 are composed of a molded thermoplastic material and as such may be presented in a wide variety of colors and surface finish textures. However, it is understood that other materials, such as, but not limited to, synthetic rubber, foamed polymers, metals, ceramics, or natural and/or synthetic textiles, may be utilized without limiting the scope of the device 10. The upper member 20 is configured to be a curvilinear polyhedron having an anterior surface 22 and a posterior surface 24. The anterior surface 22 is intended to be placed in proximity to the interior of a user's upper lip. The posterior surface 24 is configured to conform to a range of sizes encompassing users of a certain size range and be provided with any feature, including embossing or other surface texturing as may beneficially accomplish the securement of the device 10 within the intended cavity of use. The upper member thickness 36 is configured to be the amount of constituent material comprising a distance between the anterior surface 22 and the posterior surface 24. In various embodiments the upper member second thickness 36 is approximately five ten-thousandths of an inch (0.05 in) and the upper member first thickness is approximately four-and-one-half tenths of an inch (0.45 in), although these thicknesses may vary.

The upper member 20 is configured to have a first end 32 defining a lateral margin thereof and a second end 34 at an opposite lateral boundary. The length 38 of the upper member 20 is the distance between the first end 32 and the second end 35. In various embodiments the length 38 of the upper member may vary from approximately one-half of an inch (½ in.) to approximately two-and-one-quarter inches (2¼ in.). The first end 32 and the second end 34, in a preferred embodiment, are configured to be provided with an arcuate profile such that a greater amount of material is disposed along the midline of the length 38 and a lesser amount of material along an upper edge 26 and a lower edge 28. The distance between the upper edge 26 of the upper member 20 and the lower edge 28 is the upper member height 42. In a preferred embodiment, the upper member height 42 is configured to flare out from some reduced magnitude at the upper edge 26 to an increased girth along the longitudinal centerline between the anterior surface 22 and the posterior surface 24. Some embodiments may include a corresponding reduction in girth between the longitudinal centerline and the lower edge 28 of the upper member 20.

Attached to, and extending from, a center point of the lower edge 28 is the stem 50. A stem first end 55 is attached at the lower edge 28 and extends to a stem second end 56. The stem 50 is configured to be of a sufficient stem height 58, from the stem first end 55 to the stem second end 56, so as to protrude from a user's mouth even when the upper member 20 is placed in position for use. The stem second end 56 is configured to have a semicircular, or at least arcuate, profile. The user may grasp the stem second end 56 to maneuver the device 10. The stem 50 may be formed simultaneously with the upper member 20 as a single piece, or may be attached in a subsequent process to share a common anterior surface 22 and a common posterior surface 24. The stem 50 is a linear polyhedron having a stem thickness 52, configured to be the material between the anterior surface 22 and the posterior surface 24, and a stem width 54 defined as the distance between the lateral edges of the stem 50. In various embodiments the height 56 of the stem 50 may vary from approximately one-half of an inch (½ in.) to approximately three inches (3 in.) without limiting the scope or the intent of the device 10. The stem thickness 52 and the stem width 54 may be of any suitable dimension to accomplish the function of the device. In various embodiments the stem thickness 52 may be approximately five ten-thousandths of an inch (0.05 in.) to four-and-one-half tenths of an inch (0.45 in) while the stem width 54 may be approximately one-half of an inch (½ in) to approximately two-and-one quarter inches (2¼ in.).

In some embodiments, one (1), or more of the components 20, 50 of the device 10 may be water soluble, such solubility taking a sufficient period of time for the device 10 to be effective in terminating the epistaxis. After that period of time, the device 10 is envisioned to be absorbed or swallowed so as to minimize the amount of material to be disposed of by a user. Such substances may include gelatinous sugar mixtures, such as those found in some candies, or other foodstuffs. The precise chemical composition may be tailored to provide a device 10 which can meet the application period requirements, while still being edible by the user once the symptoms have been alleviated.

Referring now to FIG. 6, an isometric view of the apparatus 100, according to an alternate embodiment of the present invention, is disclosed. The apparatus 70 includes a generally cylindrical first member 72 having a finite first member length 74 and a suitable first member diameter 76. It is understood that other alternately shaped first members 72, such as rectangular, may also be utilized without limiting the scope of the alternate device 70. A catch 78 is configured to be attached to a central location of the first member 72 by means of a connector 82. The catch 78 is a generally spherical body having sufficient size to allow for the proper removal of the first member 72 upon the completion of the intended task while restricting the inadvertent swallowing thereof. The connector 82 is configured to be any natural or synthetic textile filament of sufficient length to protrude from the user's mouth even when the first member 72 is positioned correctly for the proper use. The first member length 74 may vary from approximately one inch (1 in.) to two-and-one-half inches (2½ in) while the first member diameter 76 may vary from approximately one-quarter of an inch (¼ in) to approximately five eighths of an inch (⅝ in.). The selection of constituent materials for the first member 72 and for the catch 78 may be the same as those for the upper member 20 of the device 10.

Figure 1:
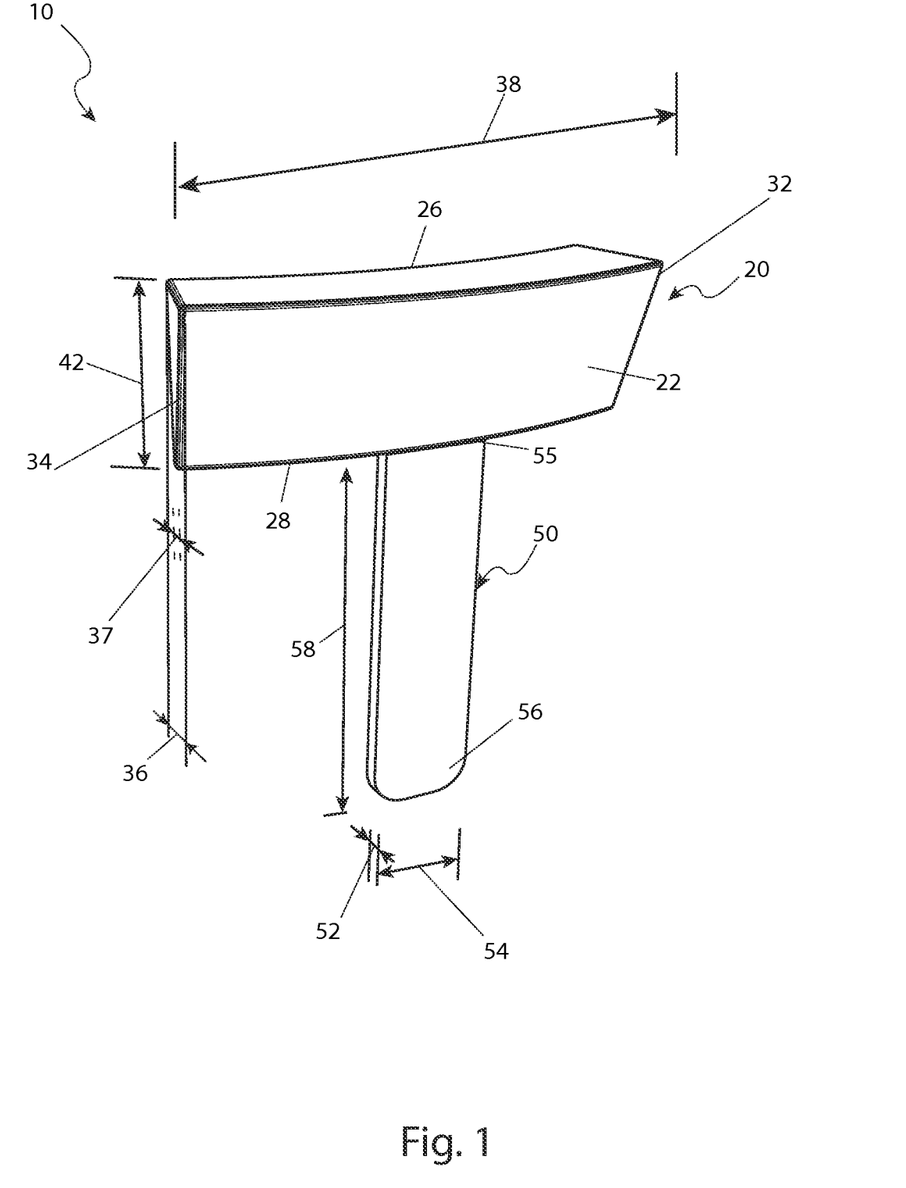
FIG. 1 is an isometric view of a nosebleed arrest implement 10 in accordance with the preferred embodiment of the present invention.
Figure 2:
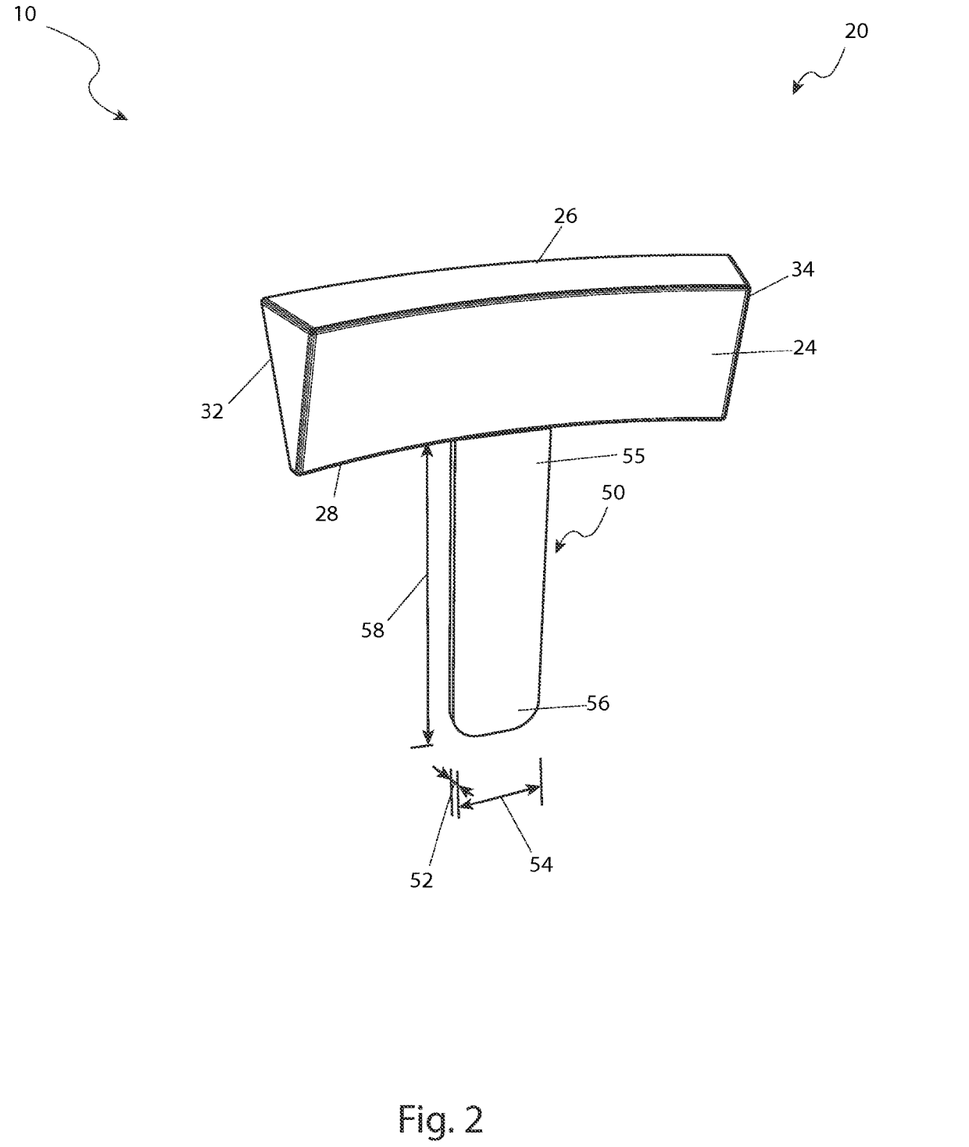
FIG. 2 is an isometric view of a posterior surface 24 of the nosebleed arrest implement 10 in accordance with the preferred embodiment of the present invention.
Figure 3:
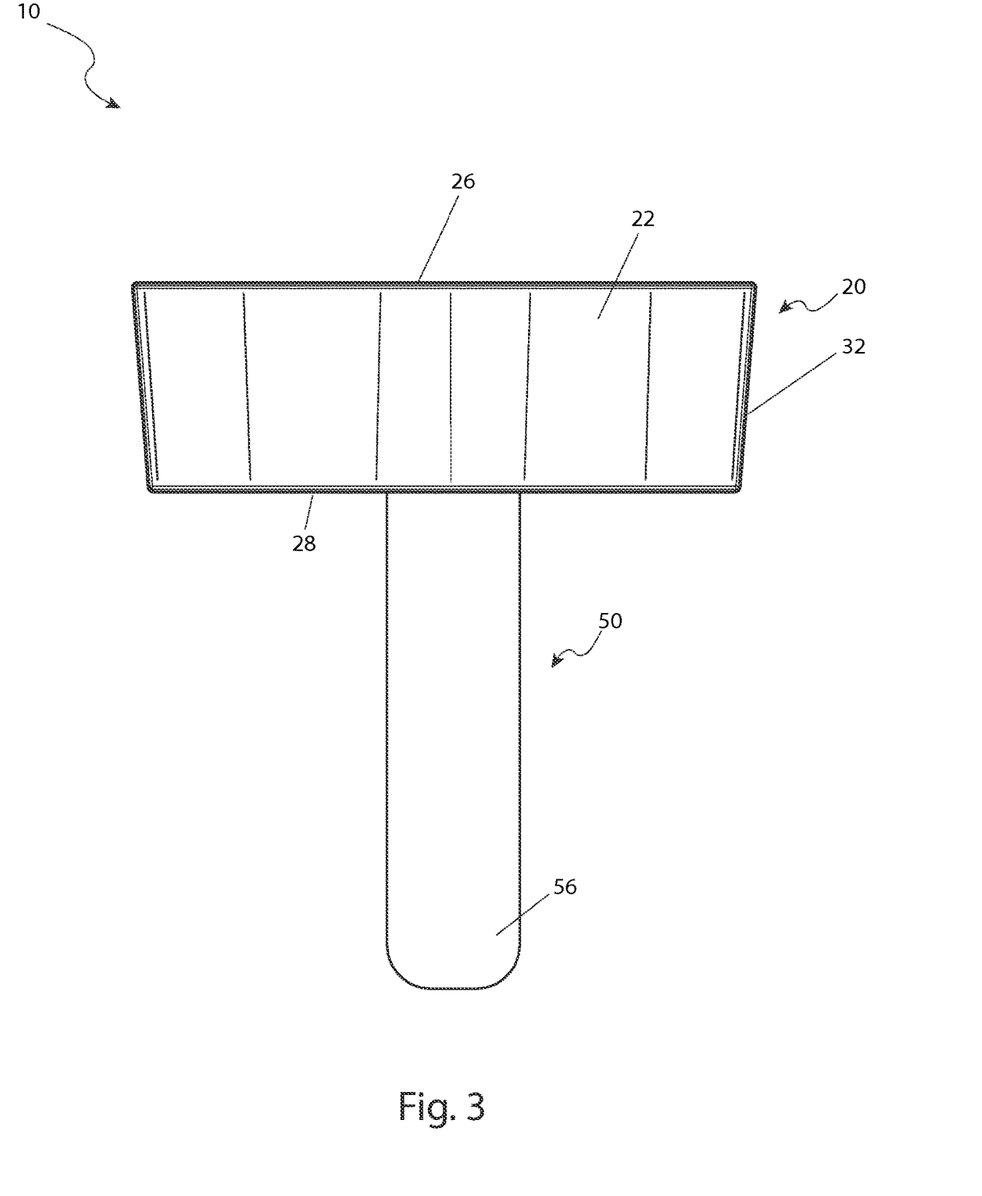
FIG. 3 is an elevation view of an anterior surface 22 of the nosebleed arrest implement 10 in accordance with the preferred embodiment of the present invention.
Figure 4:
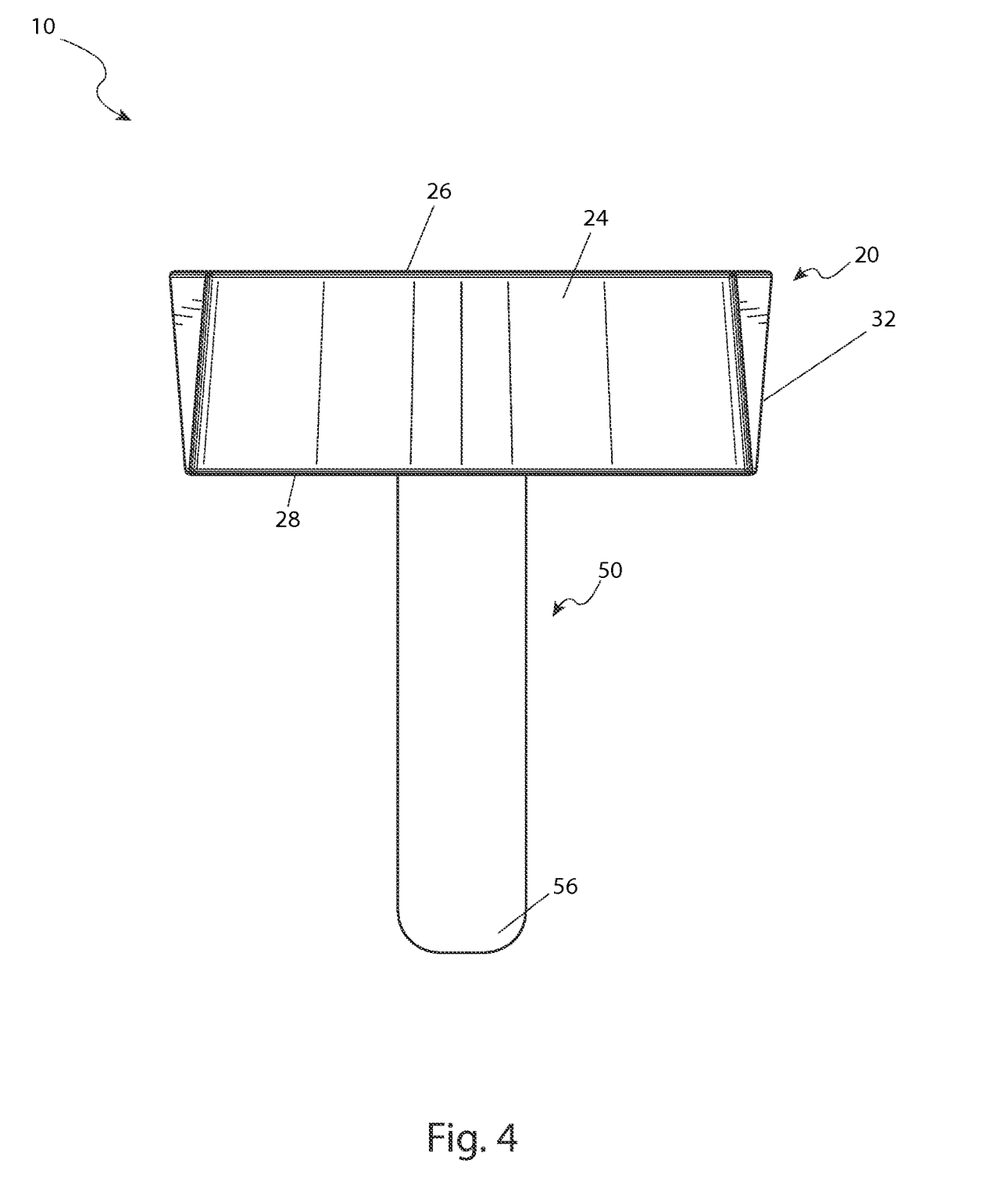
FIG. 4 is an elevation view of the posterior surface 24 of the nosebleed arrest implement 10 in accordance with the preferred embodiment of the present invention.
Figure 5:
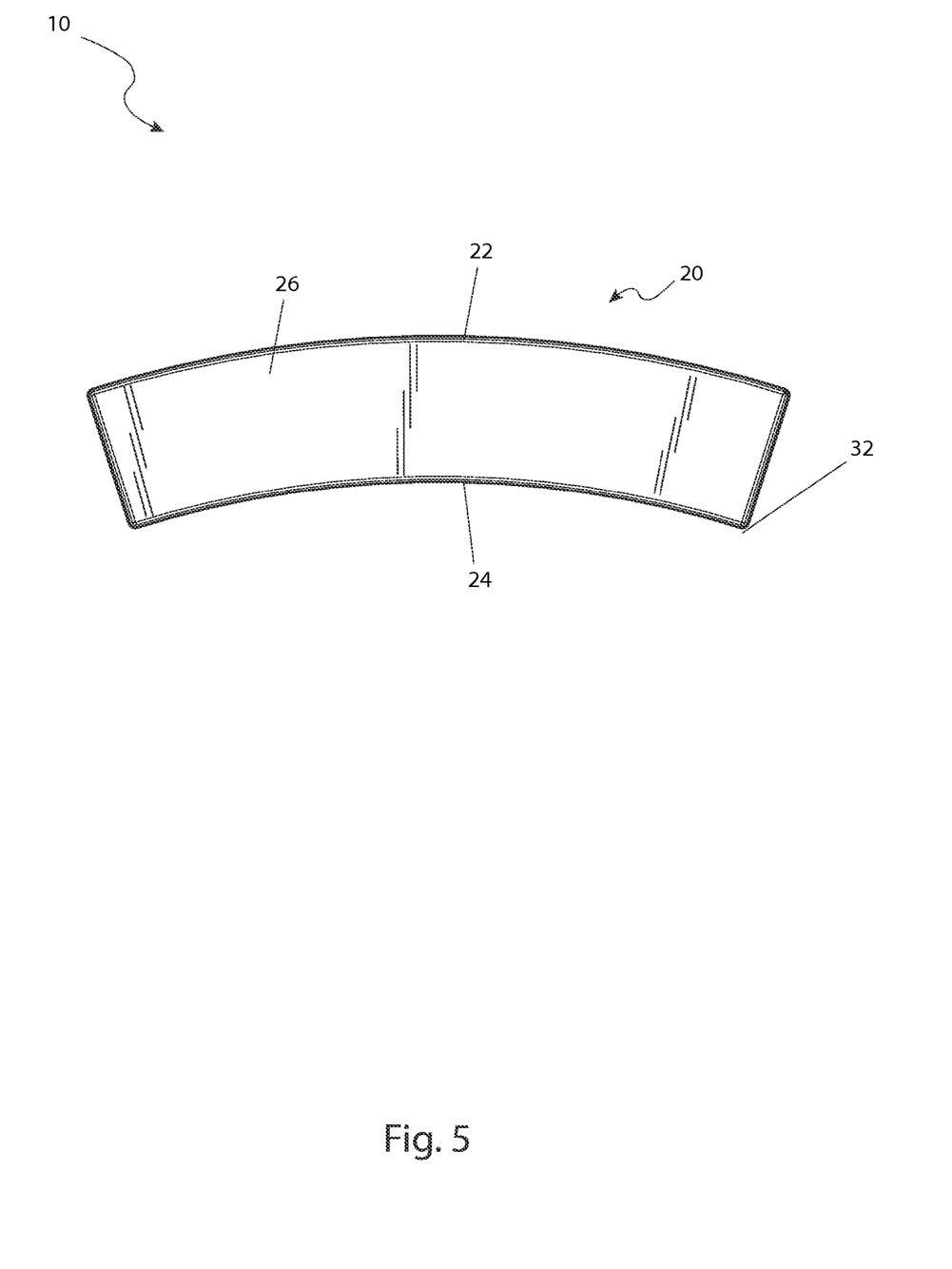
FIG. 5 is an plan view of a top of the nosebleed arrest implement 10 in accordance with the preferred embodiment of the present invention; and, FIG. 6 is an isometric view of an alternate device 80 in accordance with an alternate embodiment of the present invention.

The preferred embodiment of the present invention can be utilized by an enabled individual in a simple and straightforward manner with little or no training. After initial purchase or acquisition of the apparatus 10, it would be arranged as indicated in FIG. 1.

The method of installing and utilizing the apparatus 10 may be achieved by performing the following steps: acquiring a model of the apparatus 10 having a desired size and style to suit the taste of the user experiencing epistaxis; grasping the stem second end 56 of the stem 50 so as to competently maneuver the device 10; inserting the upper member 20 between the interior of the upper lip and the upper gum having the anterior surface 22 in contact with the upper lip and the length 38 parallel to the gum line; permitting the stem 50 to protrude from between the lips; allowing a sufficient amount or time to elapse for the hemorrhaging to cease; and removing the device 10. The device 10 may be cleaned and sterilized for reuse if the constituent material was provided for that purpose.

The alternate embodiment of the device 70, as illustrated in FIG. 6, may be utilized by performing the following steps: acquiring a model of the alternate device 80 having the desired size; grasping the first member 72; inserting the first member 72 between the interior of the upper lip and the upper gingiva having the first member length 74 aligned parallel to the gum line; permitting the catch 78 and that contiguous end of the connector 82 to protrude from the mouth; allowing a sufficient amount or time to elapse for the hemorrhaging to cease; and removing the device 70.

The foregoing embodiments of the nosebleed arrest implement have been presented for purposes of illustration and description. They are not intended to be exhaustive or to limit the invention and method of use to the precise forms disclosed. It can be appreciated by one skilled in the art that other styles, configurations, and modifications of the invention can be incorporated into the teachings of the present disclosure upon reading the specification and that the embodiments of the disclosed nosebleed arrest implement shown and described are for the purposes of clarity and disclosure and to limit the scope. The embodiments have been chosen and described in order to best explain the principles and practical application in accordance with the invention to enable those skilled in the art to best utilize the various embodiments with expected modifications as are suited to the particular use contemplated. The present application includes such modifications and is limited only by the scope of the claims.

What is claimed is:

1. A nosebleed arrest implement, comprising:
a water soluble upper member configured to be a curvilinear polyhedron, having an upper side, a lower side, an anterior side, a posterior side, a first end, and a second end; and,
a stem configured to be a linear polyhedron, having a stem upper side attached to and extending away from a center point of said lower side, terminating in a stem lower side, a stem anterior side, a stem posterior side, a stem first end, and a stem second end;
wherein said upper member has a first thickness between said posterior end and said anterior end at said upper side tapering to a second thickness between said posterior end and said anterior end at said lower side;
wherein said upper member has a length between said first end and said second end;
wherein said upper member has a height between said upper side and said lower side;
wherein said stem has a stem thickness between said stem posterior end and said stem anterior end;
wherein said stem has a stem width between said stem first end and said stem second end;
wherein said stem has a stem height between said first side and said second side;
wherein said implement is capable of arresting a flow of blood from a nasal cavity by application of restrictive pressure upon arterial passageways resulting from insertion of said upper member into an area of a mouth between an upper lip and a gingiva on a crest of a maxillary bone; and,
wherein said stem length is such that said stem extends away from a mouth when said implement is placed within said mouth.

2. The implement of claim 1, wherein said first thickness is approximately 0.45 of an inch and said second thickness is approximately 0.05 of an inch.

3. The implement of claim 1, wherein said length is in the range of and including approximately one-half of an inch to approximately 2¼ inches.

4. The implement of claim 1, wherein said first end and second end are configured to be an arcuate profile such that a greater amount of material is disposed along a midline of said length and a lesser amount of material along an upper edge thereof and a lower edge thereof.

5. The implement of claim 4, wherein said length is in the range of and including approximately one-half of an inch to approximately 2¼ inches.

6. The implement of claim 1, wherein said stem thickness is in the range of and is approximately 0.05 of an inch and 0.45 of an inch.

7. The implement of claim 1, wherein said stem width is in the range of and including approximately one-half of an inch to approximately 2¼ inches.

8. The implement of claim 1, wherein said stem height is in the range of and including approximately one-half of an inch to approximately three inches.

9. A nosebleed arrest implement, comprising:
a water soluble upper member configured to be a curvilinear polyhedron, having an upper side, a lower side, an anterior side, a posterior side, a first end, and a second end; and,
a water soluble stem configured to be a linear polyhedron, having a stem upper side extending away from a center point of said lower side, terminating in a stem lower side, a stem anterior side, a stem posterior side, a stem first end, and a stem second end;
wherein said upper member and said stem are configured from a unitary material;
wherein said upper member has a first thickness between said posterior end and said anterior end at said upper side tapering to a second thickness between said posterior end and said anterior end at said lower side;
wherein said upper member has a length between said first end and said second end;
wherein said upper member has a height between said upper side and said lower side;
wherein said stem has a stem thickness between said stem posterior end and said stem anterior end;
wherein said stem has a stem width between said stem first end and said stem second end;
wherein said stem has a stem height between said first side and said second side;
wherein said implement is capable of arresting a flow of blood from a nasal cavity by application of restrictive pressure upon arterial passageways resulting from insertion of said upper member into an area of a mouth between an upper lip and a gingiva on a crest of a maxillary bone; and,
wherein said stem length is such that said stem extends away from a mouth when said implement is placed within said mouth.

10. The implement of claim 9, wherein said first thickness is approximately 0.45 of an inch and said second thickness is approximately 0.05 of an inch.

11. The implement of claim 9, wherein said length is in the range of and including approximately one-half of an inch to approximately 2¼ inches.

12. The implement of claim 9, wherein said first end and second end are configured to be an arcuate profile such that a greater amount of material is disposed along a midline of said length and a lesser amount of material along an upper edge thereof and a lower edge thereof.

13. The implement of claim 12, wherein said length is in the range of and including approximately one-half of an inch to approximately 2¼ inches.

14. The implement of claim 9, wherein said stem thickness is in the range of and is approximately 0.05 of an inch and 0.45 of an inch.

15. The implement of claim 9, wherein said stem width is in the range of and including approximately one-half of an inch to approximately 2¼ inches.

16. The implement of claim 9, wherein said stem height is in the range of and including approximately one-half of an inch to approximately three inches.

* * * * *